United States Patent [19]

Davies

[11] Patent Number: 5,576,499

[45] Date of Patent: Nov. 19, 1996

[54] MEASURING AND MONITORING THE SIZE OF PARTICULATE MATERIAL

[75] Inventor: Clive E. Davies, Lower Hutt, New Zealand

[73] Assignee: Industrial Research Limited, Wellington, New Zealand

[21] Appl. No.: 318,842

[22] PCT Filed: Apr. 23, 1993

[86] PCT No.: PCT/NZ93/00028

§ 371 Date: Jan. 13, 1995

§ 102(e) Date: Jan. 13, 1995

[87] PCT Pub. No.: WO93/22652

PCT Pub. Date: Nov. 11, 1993

[30] Foreign Application Priority Data

Apr. 24, 1992 [NZ] New Zealand .............................. 242499

[51] Int. Cl.[6] ...................................................... G01L 5/10
[52] U.S. Cl. .............................. 73/861.41; 73/433; 73/861
[58] Field of Search ........................ 73/433, 861, 861.41, 73/865.5, 861.73.12.05

[56] References Cited

U.S. PATENT DOCUMENTS

| 3,494,217 | 10/1967 | Tanaka et al. | 73/865.5 |
|---|---|---|---|
| 3,545,281 | 12/1968 | Johnston | 73/865.5 |
| 3,640,136 | 2/1972 | Notle | 73/861.73 |
| 4,095,473 | 6/1978 | Batchelor et al. | 73/433 |
| 5,309,769 | 5/1994 | Yamakita | 73/861 |

FOREIGN PATENT DOCUMENTS

| 1485750 | 2/1972 | Australia. |
|---|---|---|
| 1068773 | 1/1984 | U.S.S.R.. |
| 1112412 | 5/1968 | United Kingdom. |
| 1429879 | 3/1976 | United Kingdom. |
| 1485750 | 9/1977 | United Kingdom. |
| 2241789 | 9/1991 | United Kingdom. |

OTHER PUBLICATIONS

Beverloo, Leniger and Van de Velde, The flow of Granular Solids Through Orifices, Chemical Engineering Science, 1961, vol.15, pp. 260–269.

Primary Examiner—Richard Chilcot
Assistant Examiner—Max H. Noori
Attorney, Agent, or Firm—Thomas R. Vigil

[57] ABSTRACT

The apparatus and method for measuring and monitoring the characteristic diameter of a flowing particulate material comprises: a chamber having a particle size measurement outlet of known dimensions through which some or all of the flowing material passes, a mechanism to determine the flow rate of the material through the particle size measurement outlet, a mechanism for determining the bulk density of the material and a mechanism to compute the characteristic diameter from the known or determined parameters.

24 Claims, 5 Drawing Sheets

MEASURING AND MONITORING THE SIZE OF PARTICULATE MATERIAL

TECHNICAL FIELD

The invention comprises an apparatus and method for measuring a diameter that characterizes the size of particulate material that is caused to flow through the apparatus, or for monitoring changes in the characteristic particle size.

BACKGROUND

Where particulate materials such as powdered or granular materials are processed, stored, packaged or the like, it is often desired to monitor the particle size of the particulates.

It is known that the rate of flow of particulate material through an orifice is determined by a number of factors including the bulk density of the material, the size of the orifice or slot, and the size of the particles. Various mathematical formulae have been put forward to describe the relationship between the parameters that affect flow rate. An equation to describe the flow rate of particles through a circular horizontal orifice in the bottom of a flat bottomed container was published by Beverloo, Leniger, and van de Velde, in the Journal, Chemical Engineering Science, volume 15, 1961. This formula is $$m_{hf} = Keg^{1/2}(D - k_h d)^{5/2} \quad (1)$$

where $m_{hf}$ is the flow rate through a horizontal orifice in a container with a flat bottom, K is a constant found by Beverloo et al to be 0.58 for agricultural seeds and sand grains and similar but which may show some small variation from material to material, which may be determined by experimentation, e is the bulk density of the material; g is acceleration due to gravity; D is the diameter of the orifice; d is the characteristic diameter of the particles; and $k_h$ is a parameter that is related to particle size.

When the bottom of the container is not flat, the flow rate can be described by similar formulae. For example, N P Cheremisinoff and P N Cheremisinoff writing in "The Encyclopedia of Fluid Mechanics", volume 4 in "Solids and Gas-Solids Flows", which is published by Gulf Publishing Company, Houston, Tex., U.S.A., have given a formula for the flow rate through a container with a conical bottom; the formula follows the approach taken earlier by Rose and Tanaka who published their work in Engineer, volume 208, 1959. Rose and Tanaka proposed that the effect of a conical bottom on a container can be accounted for by a correction factor $(\tan \alpha \tan \theta)^{-0.35}$, where $\theta$ is the angle of inclination of the hopper wall to the vertical, and $\alpha$ is the angle of repose of the granular material. N P Cheremisinoff and P N Cheremisinoff stated that the correction factor suggested by Rose and Tanaka can be applied to equation 1 giving a formula for the flow rate $m_{hc}$ of a granular solid through a circular opening in the bottom of a container with a conical bottom:

$$m_{hc} = Keg^{1/2}(D - k_h d)^{5/2} (\tan \alpha \tan \theta)^{-0.35} \quad (2)$$

$(\pi/2 - \alpha)$ should be larger than $\theta$.

It will be appreciated by those skilled in the art that there some restrictions on the use of this formula, such as when the ratio of the diameter of the container to the diameter of the orifice is small for example, and proper care and caution should be taken when the formula is used.

The effect of particle size on flow rate from containers with conical bottoms is similar to the effect on flow rate from containers with flat bottoms.

DISCLOSURE OF INVENTION

The present invention provides apparatus and method which enables a characteristic diameter of a flowing particulate material to be monitored or measured.

In broad terms the invention comprises apparatus for monitoring a characteristic diameter of a flowing particulate material, comprising a chamber having a particle size measurement outlet of known dimensions through which the flowing material or a part thereof passes, means to determine the flow rate of the material through the particle size measurement outlet, and means to determine the characteristic diameter of the material by reference to the dimensions of the particle size measurement outlet, the bulk density of the material, and the flow rate of the material.

If the particle size measurement outlet size D is known and the flow rate m through the outlet is measured, and the bulk density e of the material is known or is measured, and the factor $k_h$ is known, then the characteristic diameter d of the flowing material can be found using an equation such as equation 1 or 2 above or a variation thereof.

In broad terms in another aspect the invention comprises a method for monitoring a characteristic diameter of a flowing particulate material, comprising causing the flowing material or a part thereof to pass through a particle size measurement outlet of known dimensions, determining the flow rate of the material through the particle size measurement outlet, and determining the characteristic diameter of the material by reference to the dimensions of the particle size measurement outlet, the bulk density, and the flow rate of the material.

The outlet orifice of dimension D may be a horizontal orifice in a flat bottom such as a circular orifice or orifice of another shape, or may be a vertical orifice such as a circular orifice in a vertical wall or a closed slot orifice in a vertical wall, or similar. The orifice may be part way between vertical and horizontal.

Flow Rate Measurement—Slot Flow Measurement

Preferably to simultaneously measure the flow rate of the material the means to determine the flow rate of material comprises a second chamber having an outlet for measurement of flow rate from the second chamber through which the flow of material or a part thereof also passes, the flow rate measurement outlet being of known dimensions across the flow and of a height such that the height of the material flow through the flow rate measurement outlet will not reach the full height of the outlet over the range of flow rates to be measured, and the apparatus comprises means for determining by reference to the height of material flow through the flow rate measurement outlet the flow rate of the material.

In this most preferred form of the apparatus of the invention the outlet orifice in the second chamber is preferably a substantially constant and relatively narrow width over its height, so as to be in the form of a slit or slot for example. The height of the outlet orifice from the second chamber is such that the height of the material flow through the outlet orifice will not reach the full height of the orifice over the range of flow rates to be measured. The outlet orifice is thus termed an "open" orifice i.e. the top of the orifice does not, under normal flow conditions, limit the height of the flow of material from the orifice. For example, where the chamber in the wall of which the orifice is formed is a volume having a closed base and open at its top, the orifice may be a slot extending the full height of the side wall of the chamber. In other arrangements the slot could be closed at its top edge but the height of the orifice would then be chosen in relation to the flow rates to be encountered such that the height of the flow of material through the orifice would not reach the full height of the orifice itself, so that for all intents and purposes the aperture may be regarded as an "open" aperture. This is in contrast to a "closed" outlet orifice, from the first chamber into the second chamber for example, where the height of the outlet orifice is such that the material flow will always completely fill the orifice so that the flow is limited by the dimensions of the orifice.

The flow rate of a particulate material through such an "open" orifice can be correlated with the height of the flow of material through the orifice. Where the orifice is a slit or slot or the like which is of constant width over its height, and the slit or slot is relatively narrow in width, the flow rate of material through the slit approaches linear proportionality to the height of the material flow through the slit. Thus, the instantaneous flow rate of material may be determined by reference to the height at any instant of the flow of material through the outlet slot, of the second chamber.

In the most preferred form of the apparatus of the invention referred to above which uses a second chamber with an "open" slot outlet or similar to determine the material flow rate, this outlet slot or similar orifice preferably extends vertically, but it is possible for the aperture to be tipped either sideways or forward or rearwardly to some extent. There may also be more than a single outlet aperture from the chamber through which the flow of material passes e.g. two or-more parallel slots. As stated the outlet orifice may be of constant width over the height of the orifice but an orifice of increasing or decreasing width with height or of other shapes such as an elliptical outlet could be used because in any case a relationship between flow rate and flow height can be found, if not necessarily linear. It is also possible that the outlet "orifice" rather than comprising a single slit or slot or the like, could consist of a series of smaller holes or openings spaced heightwise in the wall of the chamber. The series of holes or openings need not be in the same vertical plane.

To determine the flow height and thus the flow rate from the outlet in the second chamber any suitable arrangement may be employed such as capacitance techniques where the flow of material acts as a dielectric in a capacitance measuring arrangement or optical sensing apparatus for monitoring the height of the flow of material, for example. Alternatively the height of the material flow through the slot outlet at any instant may be determined by reference to the weight of the material in the chamber. When the flow rate through the slot outlet is relatively high, the height of the material flow through the slot will be high and the volume of material in the chamber behind the slot will be high, so that the weight of material within the chamber will be relatively high. Conversely, when the flow rate of material is relatively low, the height of the material flow through the slot will be relatively low, so that the weight of material within the chamber behind the slot will be low. As stated, the slot need not be of constant width across the slot and for slots or outlet apertures of non-constant width a correlation between the height of the material flow through the slot or aperture and the material flow rate may still be found in any case.

In the form of the apparatus comprising two cheers one of which has an "open" outlet for flow rate measurement as described above, a flow of the particulate solids, the particle size of which is to be monitored, is directed into the first chamber which has a "closed" outlet orifice of known dimensions. The solids flow through the outlet in the first cheer into the second chamber which has an outlet orifice in the form of an "open" slot as described above. The size D of the outlet from the first chamber is known, the flow rate m from the outlet is measured with reference to the flow through the open slot of the second cheer for example from a load cell supporting the second chamber, the bulk density e of the material is known or is measured, for example by arranging a feed cell to maintain a constant volume of material in the first chamber and a load cell to monitor the weight indicative of the bulk density, and thus the particle size can be determined. The flow rate of material through a closed rectangular vertical slot can be found by an equation of the form given in equation 3, published by Davies and Foye in 1991 in the Journal, Transactions of the Institution of Chemical Engineers, Volume 69, Part A, pages 369 to 373.

$$m_{cs} = K(L-l)(W-w)\left[\frac{4(L-l)(W-w)}{2(L-l)+2(W-w)}\right]^{1/2} \quad (3)$$

where $m_{cs}$ is the flow rate of the particulate solids through the closed slot, K is a parameter that is related to the bulk density of the particulate solids and to other physical properties of the particulate solids, L is the length of the slot, W is the width of the slot, l is a parameter related to the mean characteristic size of the particles and may be expressed as $k_l d$, where d is a characteristic mean diameter of the particles, and w is also a parameter related to the mean size of the particles and may be expressed as $k_w d$.

The flow rate of material through an open slot obeys an equation that has the same form as equation 3 for flow in closed slots, provided due care and caution is taken to ensure that the solids do not approach the slot with a velocity that is excessively high (for example by using a baffle or baffles upstream of the slot).

The equation for flow in open slots $m_{os}$ is written in terms of the height of solids in the open slot, h, and is $$m_{os} = K(h-l)(W-w)\left[\frac{4(h-l)(W-w)}{2(h-l)+2(W-w)}\right]^{1/2} \quad (4)$$

The flow parameters K, l and w have similar values as for flow in closed slots.

Flow Measurement—Other Techniques

The flow rate of the particulate material can be determined by techniques other than measurement of flow rate using an open slot or other open orifice.

For example flow rate can be measured by measuring the impact force on an obstacle such as a plate placed in the path of a stream of falling particles; there are a variety of proprietary flow measurement devices available that work on this basis. The flow rate can also be found by loss-in-weight methods; the flow rate is found by measuring the rate of change of weight of a container that is mounted on load cells, for example. The material being metered either flows into the container, or out of the container. When this method is used, it is necessary to interrupt the metering process from time to time to either refill or to empty the container; there are a variety of proprietary devices available for measuring the flow rate of particulate materials by the loss-in-weight method.

Any other suitable technique for determining flow rate may be used.

Bulk Density Measurement

Preferably the apparatus comprises means to determine or monitor the bulk density of the material passing through the particle size measurement, but it is also possible that a bulk density figure or approximation may, instead of being continuously or periodically measured, be resident or programmable into software. This may particularly be possible where large swings in bulk density are not expected to be encountered in normal operation.

Where any vessel or chamber forming part of the apparatus of the invention contains a constant volume of the flowing material, the density of the material may be determined by reference to the weight of this constant volume chamber i.e. variations in the weight of the contents of the constant volume chamber will be indicative of variations of the density of the material. For example, in the most preferred two chamber apparatus described above where flow rate is determined using slot flowing measurement out of the second chamber, a feed cell may be provided prior to the chamber containing the particle size measurement outlet which feed cell acts to ensure that the first, particle size measurement chamber always contains a constant volume of material. The density of the material may then be determined by reference to the weight of the contents of this vessel.

In another arrangement where the flow rate from the particle size measurement outlet is determined not using slot flow measurement techniques but by some other flow rate measurement system for example an impact plate below the particle size measurement outlet, again a feed cell may be provided above the particle size measurement chamber to ensure that the chamber always contains a constant volume of the flowing material and density variation may be determined by reference to weight variation of this chamber.

Other density measurement techniques may also be used as follows such as the gamma ray technique for example.

PARTICLE SIZE CALCULATION

The effect of the characteristic diameter can be determined with the most preferred two chamber apparatus of the invention described above i.e. a first chamber disposed so that material flows from a "closed" slot outlet relative to the flow and of known dimensions, into the second chamber having an outlet comprising an "open" slot for flow rate measurement, as follows. The apparatus is arranged so that material flows into the first chamber at a rate that maintains material in the chamber such that the flow rate out of the closed slot is determined by the dimensions of the slot. The dimensions of the outlet slot from the first chamber are chosen so that its length, $L_1$, is much greater than its width $W_1$. The width of the open slot outlet from the second chamber is $W_2$, and $W_2$ is chosen to be different from $W_1$. The width $W_2$ and height of the open outlet slot from the second chamber is chosen so that the flow height $h_2$ will under operating conditions be much greater than $W_2$.

When equation 3 is rewritten in the form shown in equation 5, it is apparent that when $(W-w)/(L-l)$ is small, as is the case when L is much greater than W, as a good approximation equation 1 can be simplified to equation 6. Likewise equation 4 can be simplified to equation 7 to describe the flow in a narrow open slot.

$$m_{cs} = K(L-l)(W-w) \left[ \frac{4(W-w)}{2+\frac{(W-w)}{(L-l)}} \right] \quad (5)$$

$$m_{cs} = \sqrt{2} \; K(L-l)(W-w)^{3/2} \quad (6)$$

$$m_{os} = \sqrt{2} \; K(h-l)(W-w)^{3/2} \quad (7)$$

Parameter l is small, so when h or L have large values, can be neglected without introducing much error. W is related to the characteristic diameter of the particles and can be written as $w=k_w d$, so that equation 6 and equation 7 can be rearranged to express d in terms of known or measurable quantities which is done in equation 8.

$$d = \frac{\left[ W_2 \left[ \frac{h_2}{L_1} \right]^{2/3} - W_1 \right]}{k_w \left[ \left[ \frac{h_2}{L_1} \right]^{2/3} - 1 \right]} \quad (8)$$

In recent experiments it has been found that when K and $k_w$ are calculated from experimental measurements, assuming that $l=0$, $k_w$ has a value of about 1.8.

If the outlet of dimension D is other than a vertical slot, for example a horizontal circular outlet or an outlet of other shape, an equation relating d to measurable or known parameters can again be found, but will be different from equation 8.

Where the flow rate is determined other than by reference to the flow through the open slot outlet of a second chamber after the particle size measurement outlet, such as by an impact meter or by a loss in weight meter for example, the characteristic particle size can be calculated from rearrangement of the appropriate flow equation. When the flow is from a circular orifice in a flat bottomed container for example, the appropriate flow equation is equation 1, and this can be rearranged to give $$d = \frac{1}{k_h} \left[ D - \left( \frac{m_{hf}}{0.58 \; eg^{1/2}} \right)^{2/5} \right] \quad (9)$$

When the flow is from a circular orifice in a container with a conical bottom, for example, the appropriate flow equation is equation R, and this can be rearranged to give $$d = \frac{1}{k_h} \left[ D - \left( \frac{m_{hc}}{0.58 \; eg^{1/2}(\tan\theta\tan\alpha)^{-0.35}} \right)^{2/5} \right] \quad (10)$$

DESCRIPTION OF THE DRAWINGS

The invention will be further described with reference to the accompanying drawings by way of example and without intending to be limiting. In the drawings.

DETAILED DESCRIPTION

Figure 1:
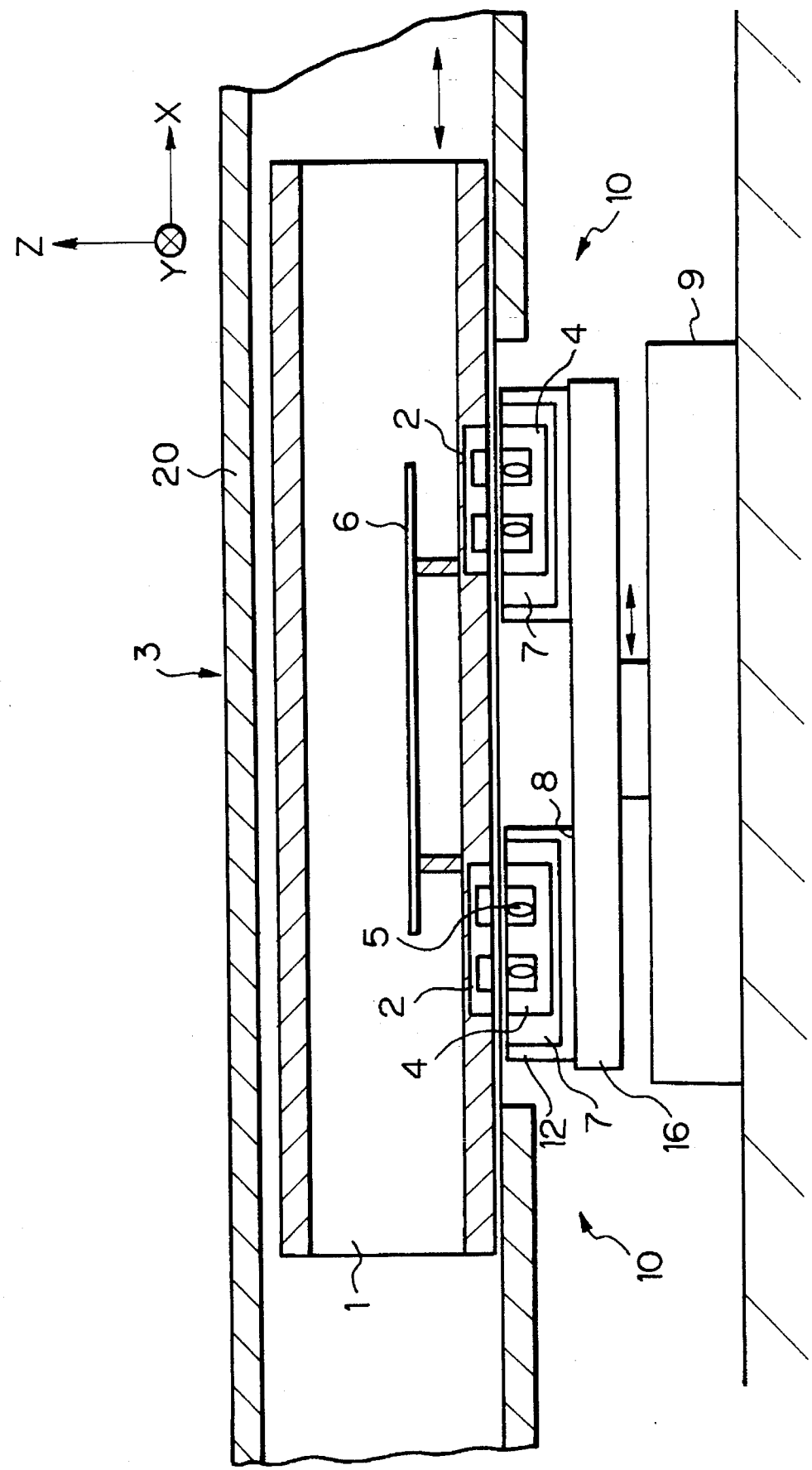
FIG. 1 is a side view diagrammatically illustrating operation of a first form of apparatus of the invention using density measurement by reference to the weight of the vessel comprising the particle size measurement outlet and flow rate measurement by a loss-in-weight flow meter above.

In the first form of apparatus of FIG. 1, a vessel defining a chamber 1 with a particle size measurement outlet orifice 2 of known dimension at the bottom is mounted by way of one or more load cells 3. The outlet orifice 2 is in a conical bottom but a flat bottom could be used. The chamber 1 receives a flow of particulate material from a feed vessel 4 mounted above the particle size measurement chamber 1. The containers defining chamber 1 and feed vessel 4 are positioned with their longitudinal axes coincidental or in some other relative position that, having regard to the angle of repose of the converging sides of the top of material in the chamber 1, the flow rate out of the particle size measurement outlet 2 from the chamber 1 will be the same as the flow rate into the chamber 1 from the feed vessel. The chamber 1 with the particle size measurement outlet 2 will then contain a constant volume of flowing material so that the weight of the vessel 1 and contents as indicated by the load cells 3 will be indicative of the bulk density of the material. The bulk density may be calculated by a microprocessor and preprogrammed look up table of weight versus density or otherwise calculated. The feed vessel 4 is also mounted on one or more load cells 5 so that it functions as a loss-in-weight flow rate measurement device. Because the flow rate through the feed vessel 4 is the same as the flow rate out of the vessel 1 therefore the flow rate out of the flow rate measurement orifice 2 is known. If the value of the parameter $k_h$ is known, then a value of the characteristic diameter d can be found and continuously calculated using equation 9 if the angle of repose α or an approximation thereof, and the angle θ for the vessel 1 are known. The calculation can be carried out automatically and continuously using a micro-processor or computer or similar.

Figure 2:
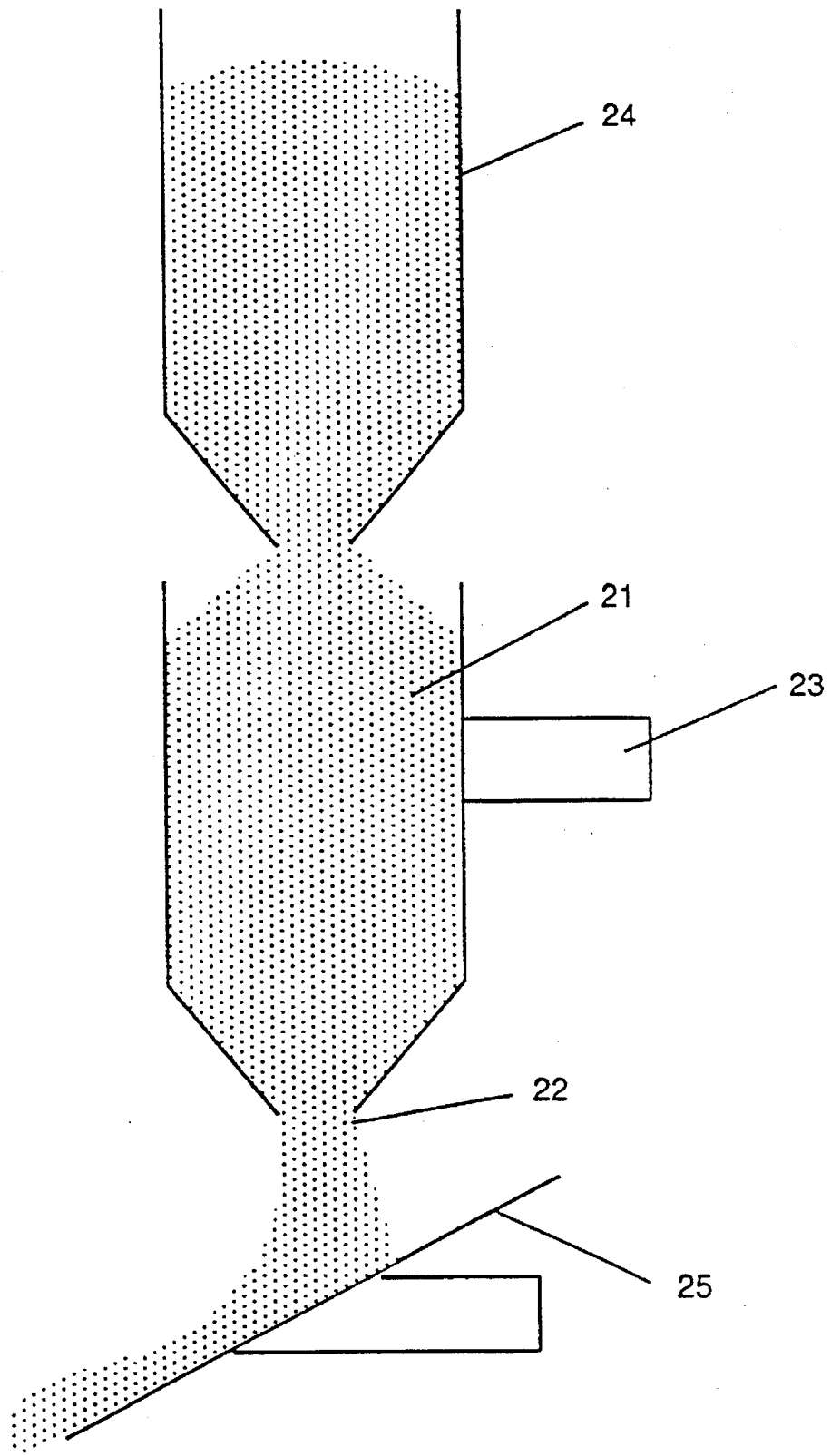
FIG. 2 is a side view diagrammatically illustrating operation of a second form of apparatus of the invention.

FIG. 2 shows a similar form of apparatus of the invention wherein the material flow rate is determined using the flow impact principle. A vessel 21 similar to vessel 1 in FIG. 1 is carried by a load cell 23 and has a particle size measurement outlet orifice 22 of known dimension. A feed vessel 24 is positioned similarly to the feed vessel 4 in FIG. 1 to maintain a constant volume of flowing material in the vessel 21. To determine the flow rate of material from the particle size measurement orifice 22 the flow of material from the orifice 22 contacts the impact surface of impact flowmeter 25. The load cells 23 indicate the weight of the vessel 21 and contents from which the density of the contents can be calculated. Again as before a microprocessor or similar is arranged to calculate the characteristic diameter d from the flow rate and density inputs, in this case the flow rate input coming from the impact flow meter 25.

Figures 3A, 3B:
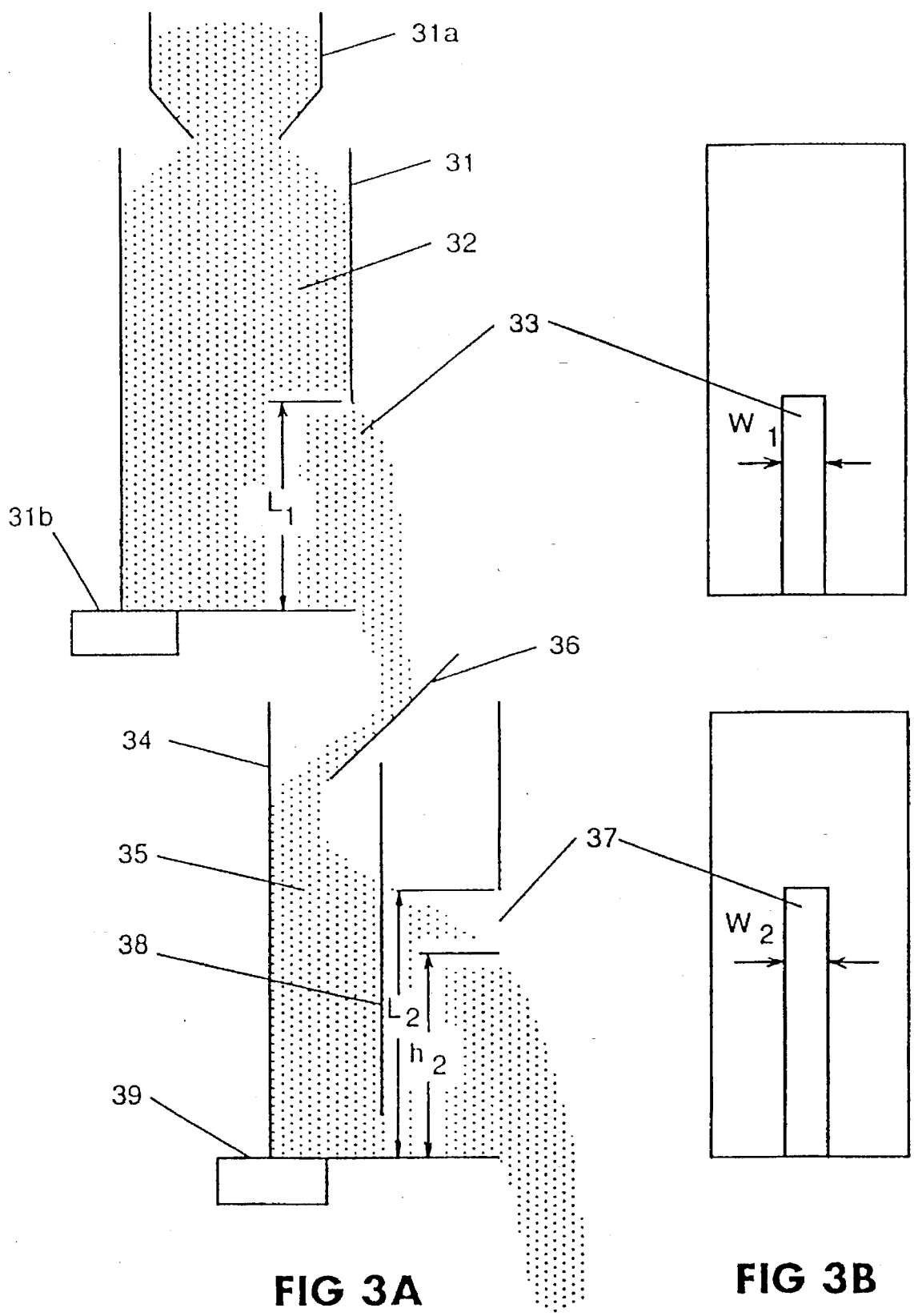
FIG. 3A is a side view diagrammatically illustrating operation of a third form of apparatus of the invention also using density measurement by reference to the weight of the vessel comprising the particle size measurement outlet and flow rate measurement by slot flow techniques from a vessel after the particle size measurement outlet.
FIG. 3B is a front view in the direction of arrow A in FIG. 3A.

FIGS. 3A and 3B show a further form apparatus of the invention. A vessel 31 defines an internal chamber 32 into which the particulate material is directed. A particle size measurement outlet in the form of a closed slot 33 extends part of the way up the side wall of the vessel 31 as shown. The slot 33 is of constant width $W_1$ over the height of the slot and of length $L_1$. A front view of the vessel and slot 33 is shown in FIG. 3B. The flow rate of particulate material into the vessel 31 from a feed vessel 31a is arranged such that the particle size measurement slot 33 will always be completely filled with flowing material in operation. A load cell 31b indicates the weight of the vessel 31 and contents from which the density of the contents can be calculated. A vessel 34 having an internal chamber 35 receives the flow from the outlet slot 33 to measure the flow rate thereof. Material from the particle size measurement vessel 31 is preferably directed against the backwall of the vessel 34 by a deflector 36 or similar. The material then flows from the rear of the vessel towards an outlet in the form of an open slot 37 of width $W_2$. The slot 37 is open i.e. the length $L_2$ of the slot 37 is such that the whole height of the slot is never filled with flowing solids under the operating conditions for which the apparatus is designed. Within the flow measurement chamber 35 the flow path is preferably obstructed by a baffle 38 or similar which moderates the velocity of the particulate solids as they flow towards the outlet slot 37.

The height of the material flow through the flow measurement slot 37 may be determined by measurement with for example capacitance or optical means as referred to previously, or by monitoring the weight of material within the chamber 35 through a load cell 39 or other weight determining means. The size of the particle size measurement slot outlet 33 is known. The flow rate of solids from this outlet slot is the same as the flow rate from the flow rate measurement slot 37, obtained from the instantaneous weight indication of the load cell 39. If the value of the parameter $k_h$ is known, then the characteristic diameter d can be found using equation 8. Again, the calculation can be carried out automatically and continuously using a computer or microprocessor or similar.

In the apparatus of FIGS. 1 to 3, the various chambers are of circular cross-sectional shape, but other shapes of chamber such as rectangular or other multi-sided chamber volumes could alternatively be employed if easier for fabrication for example.

The particles in one or more of the vessels of the apparatus can be fluidized. Particles can be fluidized and caused to behave like a liquid by passing a stream of air upwards through the particles, from a distributor device at the bottom of the vessel. Not all particles can be fluidized in this way, and thus fluidization should be utilized only for those particles which are fluidizable, and when fluidized behave in a way similar to liquids as will be appreciated by those skilled in the art.

Figure 4:
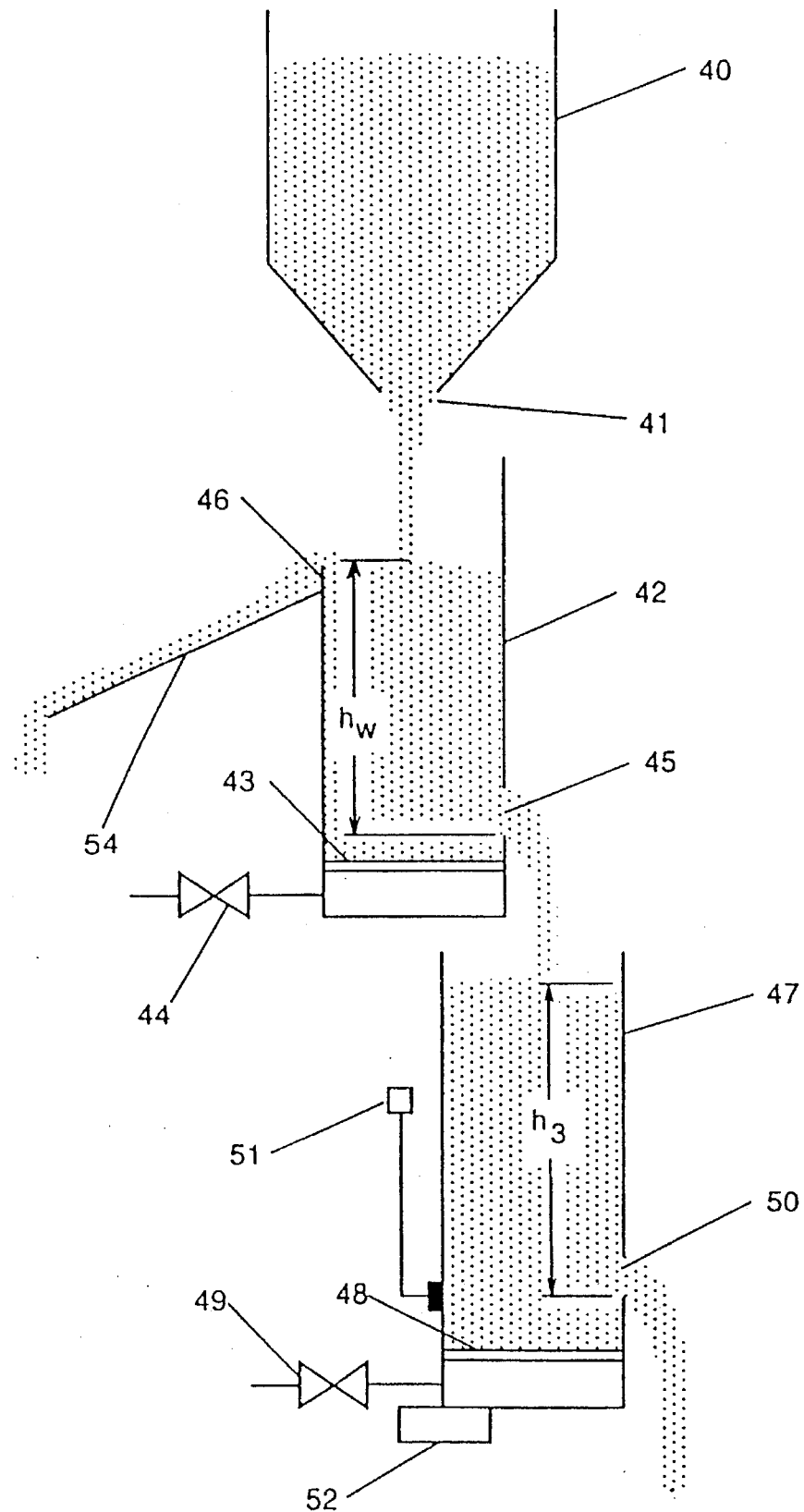
FIG. 4 is a side view diagrammatically illustrating operation of a fourth form of apparatus of the invention providing for fluidized flow of particulate material through the apparatus.

FIG. 4 shows an apparatus for estimating a characteristic diameter where the particulate solids are fluidized. The apparatus consists of three vessels through which the particulate solids flow. A first vessel 40 into which the particulate material is directed has an outlet orifice 41 located at the bottom of the chamber, which is optionally conical shape to permit free draining.

Figure 5:
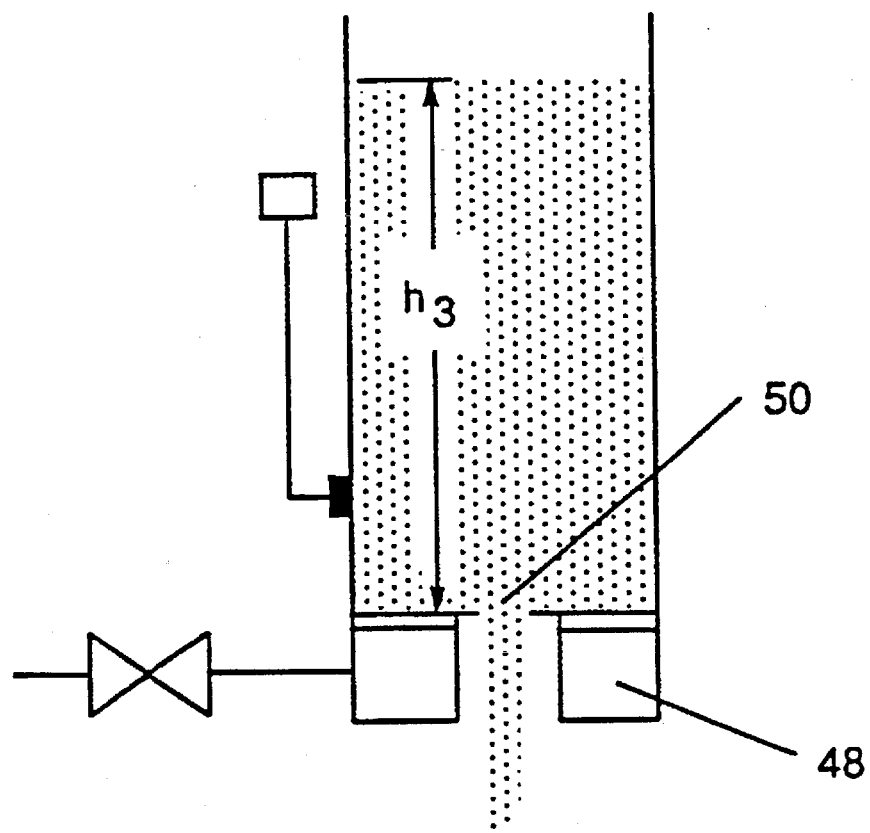
FIG. 5 diagrammatically illustrates a modification to a fluidized flow form of the apparatus of the invention to permit the outlet orifice to be located in the floor of a vessel containing fluidized solids.

A second vessel 42 receives the solids flow from the outlet 41 in the vessel 40. The vessel 42 has a distributor device 43 as its floor that enables a current of air or gas to be passed through the flowing solids in the vessel 42 causing them to be fluidized. The flow rate of the air or gas used to fluidize the solids is controlled by a valve 44. In a lower part of a wall of the vessel 42 is an outlet 45 which is preferably a slot but could be another shape such as circular. The outlet 45 can also be located in the floor of the vessel 42 or equivalent, but the design of the distributor device 43 must then be modified for example as shown in FIG. 5.

A weir 46 is located in the side of the vessel 42. Once the height of solids in the vessel 42 reaches the height of the weir 46, solids pass over the weir and the height $h_w$ of solids above the orifice 45 is kept constant. The particles that flow over the weir 46 are collected by a chute 54, which directs the particles as required. The diameter of the outlet 41 in the vessel 40 is chosen to ensure that the vessel 42 is always filled to the height of the weir $h_w$ in operation of the apparatus.

A third vessel 47 receives the solids flow from the outlet 45 in the vessel 42. The vessel 47 has a distributor device 48 as its floor so that its contents can be fluidized, as are the solids in the chamber 42. The flow rate of the air or gas used to fluidize the solids is controlled by a valve 49. In a lower part of a wall of the vessel 47 is an outlet 50 which is preferably a slot but may be another shape such as circular. The outlet 50 can also be located in the floor of the vessel 47 but the design of the distributor device 48 must then be modified, for example as in FIG. 3.

The height $h_3$ of flowing solids in the vessel 47 may be determined by direct measurement, or by indirect measurement methods. Two indirect measurement methods are particularly convenient. Height is proportional to pressure and the vessel can be fitted with pressure measurement means 51, and height can be found from the measured pressure. Alternatively, the vessel 47 can be attached to weight indicating load cell 52 and height can be found as has previously been described.

The particulate solids in the vessel 42 are maintained at a constant height $h_w$ by the action of the weir 46. As stated, the size of the orifice must be sufficiently large that the level of the fluidized particles in the chamber 42 is always at least up to the weir 46 i.e. the flow rate into the chamber 42 should be greater than the flow rate from the outlet 45. The height of the particulate solids is then at all times $h_w$. Outlet 45 is the particle size measurement outlet.

The equations that describe a fluidized flow of a powdered or particulate material will not be the same as for a non-fluidized flow but appropriate equations can be found and the method of the invention is the same. The flow rate of fluidized solids through an orifice is proportional to $h_f^{1/2}$ where $h_f$ is the height of the particles above the orifice. The effect of particle size on flow rate through an orifice is greatest for ratios of orifice diameter to particle diameter that are less than about 50. The flow rate of fluidized particles through an orifice is also proportional to the area of the orifice and the density of the particles, and when the ratio of the diameter of the orifice to the characteristic mean diameter of the particles is small, the flow rate through the orifice is reduced below the value that would be expected, by an amount that is related to the size of the particles. The flow rate out of the orifice 45 is the same as the flow rate out of the orifice 50. By measuring the way that the height $h_3$ changes, an indication is obtained of the flow rate out of the outlet 50 and thus of the way that the size of the particles is changing. If the exact mathematical form of the relationship between mean particle size and orifice diameter is known, the mean particle diameter can be calculated. Alternatively, the apparatus can be calibrated using particles of known sizes.

In the drawings separate and distinct vessels are shown, the vessels each having an opening in the form of an orifice or a slot or the like, but the vessels need not necessarily be made as separate and distinct vessels, but could be cast or made or fashioned in a single piece of equipment for example.

It will also be appreciated that whereas in the apparatus of FIGS. 1 to 4 the flow rate is determined in series with flow through the particle size measurement orifice, a flow of material could alternatively be split into two or more parts and the operation of splitting the flow could be done so that the properties and the characteristic mean particle size of each resulting part of the flow is the same. The characteristic mean size of the particles could be obtained from separate measurements on the different like parts of the flow.

In any apparatus of the invention separate read outs or other indications of bulk density and mass flow rate may be provided as well as of the particles characteristic diameter, if desired.

In any case it may be necessary to calibrate any particular apparatus and modify the values of the constants in the equations and possibly the equations themselves somewhat. The equations given are not the only equations that relate particle size to flow rate and bulk density and other equations may be used.

The foregoing describes the invention. Alterations and modifications as will be obvious to those skilled in the art are intended to be incorporated within the scope of the invention, as defined in the claims.

I claim:

1. Apparatus for monitoring a characteristic diameter of a flowing particulate material, comprising
    a chamber having a particle size measurement outlet of known dimensions through which the flowing particulate material or a part thereof passes,
    means for determining substantially continuously the flow rate of the flowing particulate material through the particle size measurement outlet, and
    means to determine the characteristic diameter of the flowing particulate material as a function of the dimensions of the particle size measurement outlet, the bulk density, and the flow rate of the flowing particulate material.

2. Apparatus as claimed in claim 1, wherein the means to determine the flow rate of material comprises a second chamber having an outlet for measurement of flow rate from the second chamber through which the flow of material or a part thereof also passes, the flow rate measurement outlet being of known dimensions across the flow and of a height such that the height of the material flow through the flow rate measurement outlet will not reach the full height of the outlet over the range of flow rates to be measured, and means for determining by reference to the height of material flow through the flow rate measurement outlet the flow rate of the material.

3. Apparatus as claimed in claim 2, wherein the means for determining the flow rate of the material through the flow height measurement outlet comprises means to determine the height of the material flow from the flow rate measurement outlet by reference to the weight of material in the flow measurement chamber.

4. Apparatus as claimed in claims 1, wherein the flow rate measurement outlet is in the form of a slit or slot.

5. Apparatus as claimed in claim 4, wherein the flow rate measurement outlet is of a substantially constant width across the outlet over the height of the outlet.

6. Apparatus as claimed in claim 2, wherein the chamber comprising the flow rate measurement outlet is positioned in series following the particle size measurement outlet to receive the flow of material from the particle size measurement outlet or a part thereof.

7. Apparatus as claimed in claim 4, wherein the particle size measurement outlet is in the form of a slit or slot of different width and height than the flow rate measurement outlet, and the characteristic diameter of the flowing material is determined substantially by reference to the equation:

$$d = \frac{W_2(h_2/L_1)^{2/3} - W_1}{k_w((h_2/L_1)^{2/3} - 1)}$$

where $L_1$ is the height of the particle size measurement outlet, $h_2$ is the height of the solids flow in the particle size measurement outlet, $W_1$ is the width of the flow rate measurement outlet, $W_2$ is the width of the particle size measurement outlet, and $k_w$ is about 1.8.

8. Apparatus as claimed in 1, including means to determine the bulk density of the material passing through the particle size measurement outlet.

9. Apparatus as claimed in claim 8, comprising means to maintain a substantially constant volume of material in the chamber comprising the particle size measurement outlet and means to determine the bulk density of the material by reference to changes in the weight of the contents of the particle size measurement chamber.

10. Apparatus as claimed in claim 1, wherein the means to determine the flow rate of the material comprises a second chamber comprising a loss-in-weight flow meter.

11. Apparatus as claimed in claim 10, wherein the flow rate measurement chamber is positioned in series with and above the particle size measurement chamber such that the flow rate measurement chamber also acts as a feed chamber to maintain a substantially constant volume of material in the particle size measurement chamber, and comprising means to determine the density of the material by reference to the weight of the contents of the particle size measurement chamber.

12. Apparatus as claimed in claim 1 wherein the flow rate is determined by an impact flow meter.

13. Apparatus as claimed in claim 12, wherein a feed chamber is positioned in series with and above the particle size measurement chamber such that the feed chamber maintains a substantially constant volume of material in the particle size measurement chamber and comprising means to determine the density of the material by reference to weight of the contents of the particle size measurement chamber.

14. Apparatus as claimed in claim 1, wherein the chamber containing the particle size measurement outlet comprises means to fluidize the material within the chamber and also means to maintain a substantially constant fluidized volume of flowing material in the particle size measurement chamber.

15. Apparatus as claimed in claim 14, wherein the means to maintain a substantially constant fluidized volume of flowing material in the particle size measurement vessel comprises a weir in the particle size measurement vessel.

16. Apparatus as claimed in claim 14, wherein flow rate is determined using a second vessel comprising means to fluidize the contents thereof and having an outlet of known dimensions and wherein the flow rate is determined by reference to the height or weight at any instant of the fluidized contents in the flow rate measurement vessel.

17. Apparatus claimed in claim 10, including means to determine the bulk density of the material passing through the particle size measurement outlet.

18. Apparatus claimed in claim 17, comprising means to maintain a substantially constant volume of material in the chamber comprising the particle size measurement outlet and means to determine the bulk density of the material by reference to changes in the weight of the contents of the particle size measurement chamber.

19. A method for monitoring a characteristic diameter of a flowing particulate material, comprising causing the flowing particulate material or a part thereof to pass through a particle size measurement outlet of known dimensions, determining, substantially continuously, the flow rate of the flowing particulate material through the particle size measurement outlet, and determining the characteristic diameter of the flowing particulate material as a function of the dimensions of the particle size measurement outlet, the bulk density, and the flow rate of the flowing particulate material.

20. A method as claimed in claim 19, including causing the material or a part thereof to pass through a second outlet for measurement of flow rate of known dimensions across the flow and of a height such that the height of the material flow through the flow rate measurement outlet will not reach the full height of the outlet over the range of flow rates to be measured, and determining the flow rate of the material by reference to the height of material flow through the flow rate measurement outlet.

21. A method as claimed in claim 20, including determining the height of the material flow from the flow rate measurement outlet by reference to the weight of material in the flow measurement chamber.

22. A method as claimed claim 20, wherein the flow rate measurement outlet is in the form of a slit or slot.

23. A method as claimed in claim 19, including determining the bulk density of the material passing through the particle size measurement outlet.

24. A method as claimed in claim 23, comprising maintaining a substantially constant volume of material in the chamber comprising the particle size measurement outlet and determining the bulk density of the material by reference to changes in the weight of the contents of the particle size measurement chamber.

* * * * *